United States Patent
Trese

[11] Patent Number: 6,083,155
[45] Date of Patent: Jul. 4, 2000

[54] EYELID SPECULUM

[75] Inventor: Michael T. Trese, Bloomfield Hills, Mich.

[73] Assignee: Nuvue Technologies, L.L.C., Westmoreland, N.H.

[21] Appl. No.: 09/293,108

[22] Filed: Apr. 16, 1999

[51] Int. Cl.⁷ .................................................. A61B 12/02
[52] U.S. Cl. .......................................... 600/236; 600/207
[58] Field of Search .................................... 600/207, 208, 600/236

[56] References Cited

U.S. PATENT DOCUMENTS

| | | | |
|---|---|---|---|
| 3,831,587 | 8/1974 | Boyd | 600/208 |
| 4,312,353 | 1/1982 | Shahbabian | 600/207 |
| 4,782,820 | 11/1988 | Woods | 600/236 |
| 4,984,564 | 1/1991 | Yuen | 600/208 |
| 5,159,921 | 11/1992 | Hoover | 600/208 |
| 5,213,114 | 5/1993 | Bailey, Jr. | 600/208 |
| 5,267,553 | 12/1993 | Graether | 600/236 |
| 5,322,054 | 6/1994 | Graether | 600/236 |
| 5,374,272 | 12/1994 | Arpa et al. | 600/236 |
| 5,433,190 | 7/1995 | Sunalp | 600/236 |
| 5,681,341 | 10/1997 | Lunsford et al. | 600/208 |

*Primary Examiner*—Paul J. Hirsch
*Attorney, Agent, or Firm*—Gifford, Krass, Groh, Sprinkle, Anderson & Citkowski, P.C.

[57] ABSTRACT

An eyelid speculum is disclosed in the form of an annular bladder constructed of a resilient material. The annular bladder defines an interior chamber and the bladder is dimensioned to fit in between the upper and lower eyelids of an eye. An inflator is fluidly connected to the bladder chamber to selectively inflate the bladder. Thus, with the bladder positioned in between the upper and lower eyelid and then inflated, the bladder maintains the eyelids in an open position thus exposing the eye and maintaining a stable eye position for medical examination and/or treatment.

6 Claims, 1 Drawing Sheet

EYELID SPECULUM

BACKGROUND OF THE INVENTION

I. Field of the Invention

The present invention relates generally to medical devices and, more particularly, to an eyelid speculum.

II. Description of the Prior Art

In order to perform many diagnostic and other medical procedures on an eye, it is necessary that the upper and lower eyelids be maintained in an open position in order to provide visual access to the eye. Many patients, particularly children, however, are unable to maintain their eyelids in an open and central position during a medical procedure due to accident, injury, physical condition or youth of the patient.

For those patients unable to maintain their eyes in an open position, it has been previously necessary to use an eyelid speculum to maintain the eyelids in an open position. The previously known eyelid speculums are typically constructed of a rigid material and include two elongated arms each having an eyelid clip at one end. The clips are positioned under both the upper and lower eyelids and the arms themselves are resiliently urged apart thus opening the eyelids. These previously known eyelid speculums, however, have not proven wholly satisfactory in use.

One disadvantage of these previously known eyelid speculums is that, since the speculum is constructed of a hard material, typically metal, the speculum can cause abrasion or other injury to the eyeball during its insertion and/or use. Furthermore, these previously known eyelid speculums were particularly difficult to use on very young patients and did not help maintain central position of the eye.

SUMMARY OF THE PRESENT INVENTION

The present invention provides an eyelid speculum which overcomes all of the above-mentioned disadvantages of the previously known devices.

In brief, the eyelid speculum of the present invention comprises an annular bladder constructed of a resilient soft material and defining an interior chamber. The bladder is dimensioned to fit, when deflated, in between the upper and lower eyelids of an eye when the eyelids are substantially closed.

An inflator is fluidly connected with the interior chamber of the bladder. Thus, when actuated, the inflator inflates the bladder into an annular shape thus moving the upper and lower eyelids to a fully open position and visually exposing the eye. A posterior flange fits into the cul-de-sac stabilizing the eye. The desired medical procedure can then easily be performed on the eye.

Since the bladder is constructed of a resilient soft material, possible injury to the eye during use of the speculum is avoided. Furthermore, the speculum of the present invention is relatively easy to use even on young patients.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
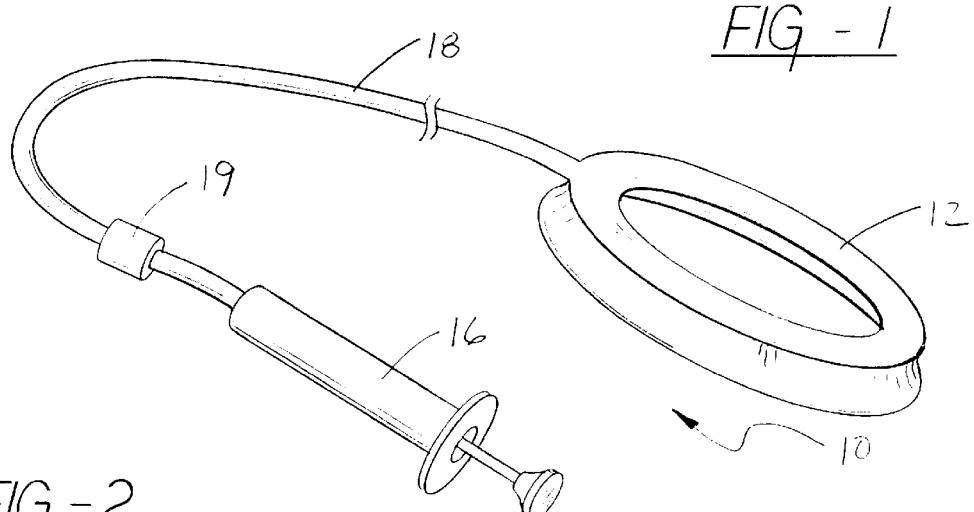
FIG. 1 is an elevational view illustrating a preferred embodiment of the present invention.
Figure 4:
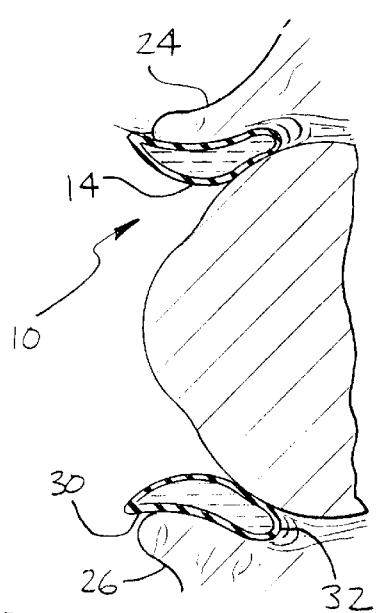
FIG. 4 is a sectional view taken substantially along line 4—4 in FIG. 3.

With reference first to FIGS. 1 and 4, a preferred embodiment of the eyelid speculum 10 of the present invention is there shown and comprises an annular bladder 12. The bladder 12 is constructed of a resilient material having an interior chamber 14 (FIG. 4) which is annular in shape.

Figure 3:
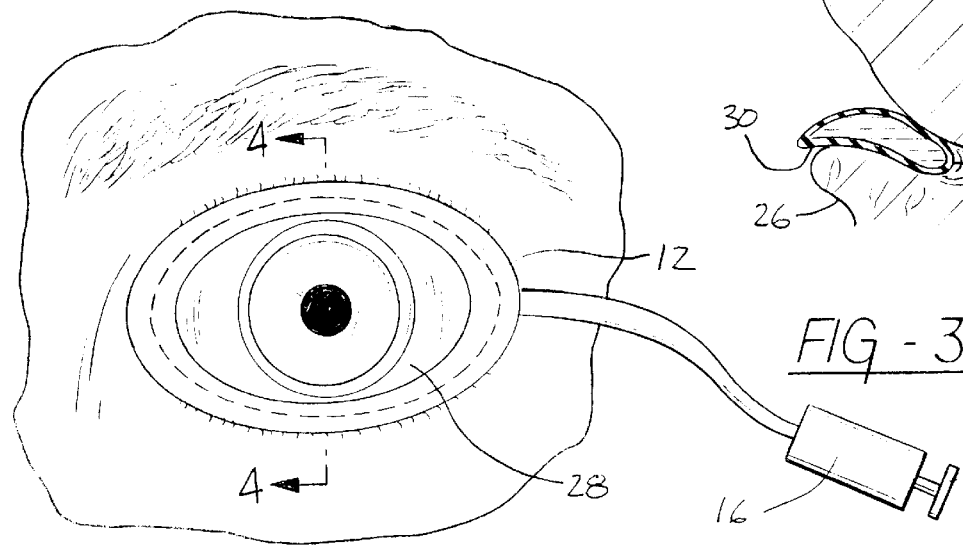
FIG. 3 is a view similar to FIG. 2 but illustrating the speculum in an inflated condition.

Referring now especially to FIGS. 1 and 3, an inflator 16 is fluidly connected to the bladder chamber 14 by a tube 18. The inflator 16 can be of any conventional design, such as a manually operated air pump, a source of fluid pressure, or even a syringe. Any conventional fluid connectors can be used to fluidly connect the inflator to the bladder chamber 14 and preferably a one-way valve 19 is fluidly connected in series between the inflator 16 and bladder chamber 14.

Similarly, any type of fluid can be used with the inflator. For example, the fluid can comprise air or water.

Figure 2:
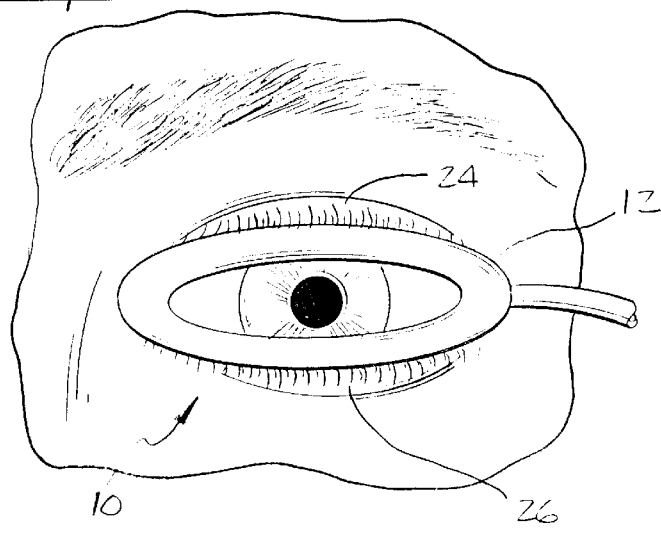
FIG. 2 is a plan view illustrating the insertion of the speculum of the present invention.

With reference now to FIGS. 2 and 4, with the bladder 12 in a deflated, collapsed condition, the bladder 12 is dimensioned so that it can be positioned in between the upper eyelid 24 and lower eyelid 26 of an eye 28 when the eyelids are in a substantially closed position. As best shown in FIG. 4, an outer periphery 30 of the bladder 12 is concave in shape so that one axial end 32 of the bladder 12 is positioned under the eyelids 26 and 24.

With reference now to FIG. 3, with the bladder 12 positioned in between the eyelids 24 and 26, the inflator 16 is actuated thus inflating the bladder 12 to the position shown in FIG. 3. In doing so, the bladder 12 moves from its collapsed state in which its sides flatly abut against each other (FIG. 2) to an annular shape (FIG. 3). In doing so, the bladder 12, since it is mechanically connected to the eyelids 24 and 26 as shown in FIG. 4, opens the eyelids 24 and 26 and maintains the eyelids 26 and 24 in an open position thus exposing the eyeball 28 through the center of the bladder 12. The required examination, diagnostic procedure or other medical procedure is then performed on the eye 28.

When use of the speculum is no longer required, the speculum can be either removed from the eye in its inflated state thus allowing the eyelids 24 and 26 to return to their normal position, or alternatively deflated and then removed.

From the foregoing, it can be seen that the eyelid speculum of the present invention provides a simple, inexpensive and yet totally effective eyelid speculum which overcomes all of the previously known problems of the prior art devices. Having described my invention, however, many modifications thereto will become apparent to those skilled in the art to which it pertains without deviation from the spirit of the invention as defined by the scope of the appended claims.

I claim:

1. An eyelid speculum comprising:

an annular bladder constructed of a resilient material and defining an interior chamber, said bladder dimensioned to fit between the upper and lower eyelids of an eye, a fluid inflator fluidly connected to said interior chamber which, upon actuation, inflates said bladder into an annular shape to move the upper and lower eyelids apart to expose the eye through a center of said bladder.

2. The invention as defined in claim 1 wherein an outer surface of said bladder is concavely shaped.

3. The invention as defined in claim 2 wherein said outer surface faces radially outwardly from an axis of said bladder.

4. The invention as defined in claim 1 wherein said inflator comprises a manually actuated air pump.

5. The invention as defined in claim 1 wherein said inflator comprises a syringe.

6. The invention as defined in claim 1 and comprising a one-way valve fluidly connected in series between said inflator and said bladder chamber.

* * * * *